United States Patent [19]

Grassetti

[11] Patent Number: 6,043,256

[45] Date of Patent: *Mar. 28, 2000

[54] ANTIMUTAGENIC AGENTS

[76] Inventor: Davide R. Grassetti, 19810 Peppermint Falls Rd., Jamestown, Calif. 95327

[ * ] Notice: This patent is subject to a terminal disclaimer.

[21] Appl. No.: 09/129,392

[22] Filed: Aug. 5, 1998

Related U.S. Application Data

[63] Continuation-in-part of application No. 08/906,466, Aug. 5, 1997
[60] Provisional application No. 60/026,118, Sep. 16, 1996.
[51] Int. Cl.[7] ..................... A61K 31/455; A61K 31/505; A61K 31/425
[52] U.S. Cl. .......................... 514/335; 514/335; 424/266; 424/251; 424/270
[58] Field of Search ............................. 552/601; 424/266, 424/270; 23/230; 514/355

[56] References Cited

U.S. PATENT DOCUMENTS

| | | | |
|---|---|---|---|
| 3,698,866 | 10/1972 | Grassetti | 23/230 |
| 4,152,439 | 5/1979 | Grassetti | 424/266 |
| 4,378,364 | 3/1983 | Grassetti | 424/266 |
| 5,608,093 | 3/1997 | Stache et al. | 552/601 |

FOREIGN PATENT DOCUMENTS

| | | | |
|---|---|---|---|
| 88302 | 2/1988 | New Zealand | 51/8 |
| 881728 | 7/1988 | New Zealand | 333/36 |
| 8907456 | 8/1989 | WIPO | 51/8 |
| 930762 | 6/1993 | WIPO | 9/107 |

OTHER PUBLICATIONS

Davis et al., In situ staining for PARP activity using and NAD analog,J.Histochem>Cytochem(1998),p46(11).
Guo et al, Inhibition of PARP rescues human T lym . . . , Toxicol. Appl. Pharmacol. p152(2), 1998.
Ariumi et al., In cico phosphorylation of PARP is ind . . . , FEBs lett. p436(2), 1998.
Ahmad et al., Hepatic–mediated elev . . . Biochem Pharmacol(england), p1697–701, May 1986.
Grassetti D.R.,Modification of external sulfhydryl . . . , Biochem Pharmacol(US), p1836–8, May 1970.

*Primary Examiner*—Keith D. MacMillan
*Assistant Examiner*—Vickie Kim
*Attorney, Agent, or Firm*—The Brotman Group; Harris F. Brotman

[57] ABSTRACT

A method of treating a human subject to inhibit mutagenic effects of carcinogens by administering to the subject a composition comprising a sufficient amount of 6,6'-dithiodinicotinic acid to inhibit activity of poly(ADP-ribose) polymerase in said subject to thereby inhibit said effects. Also provided is a method of inhibiting occurrence of mutations and of cancers derived from mutations, which method comprises administration to a subject of a composition comprising a sufficient amount of 6,6'-dithiodinicotinic acid.

4 Claims, No Drawings

ANTIMUTAGENIC AGENTS

This application is a continuation-in-part of U.S. patent application 08/906,466 filed Aug. 5, 1997, which derives priority of U.S. Provisional application 60/026,118 filed Sep. 16, 1996.

BACKGROUND OF THE INVENTION

1. Field of the Invention

This invention relates to a method for inhibiting the mutagenic effects of carcinogens, and in particular, a method for administering to a human the compound 6,6' dithiodinicotinic acid to inhibit the activity of the enzyme poly(ADP-ribose) polymerase to inhibit the occurrence of mutation-caused cancer.

2. Background of the Invention

Mutations occur in cellular DNA under the effect of ultraviolet light, infrared light, x-rays, ionizing radiation, and chemicals. It is generally accepted that most mutations lead to cancer.

The enzyme poly(ADP-ribose) polymerase (ADPRP) has been suspected to play a regulatory role in many cellular activities, including DNA repair, differentiation, and malignant transformation. Studies of inhibitors of ADPRP have provided evidence of the importance of ADPRP in those cellular activities (M. J. Suto et al., 1991, Drugs of the Future, 16:723–739). Many analogs of nicotinamide, a product of ADPRP's action on NAD, have been studied in the hope of finding a compound that could modulate the activity of ADPRP. It would be desirable to find a selective inhibitor of ADPRP which could inhibit the malignant transformation of human cells (Ibid).

SUMMARY OF THE INVENTION

It has been discovered that 6,6'-dithiodinicotinic acid has an antimutagenic effect. The method of the invention is based on the finding that 6,6'-dithiodinicotinic acid is a useful agent for the prevention of mutations, most of which lead to cancer.

The method of the invention comprises treating a human subject to inhibit the mutagenic effects of carcinogens. The method involves administering to the subject a composition comprising a sufficient amount of 6,6'-dithiodinicotinic acid to inhibit the activity of poly(ADP-ribose) polymerase to thereby inhibit the mutagenic effects, and in particular, their carcinogenic effects. In another aspect, the invention involves a method of inhibiting the occurrence of mutations and of cancers derived from mutations, and involves administering to a subject a composition comprising a sufficient amount of 6,6'-dithiodinicotinic acid.

DETAILED DESCRIPTION OF THE INVENTION

General Description and Definitions

The practice of the present invention will employ, unless otherwise indicated, conventional molecular and cell biology, cell culture, biochemistry, and organic and medicinal chemical synthesis within the skill of the art. Such techniques are explained fully in the literature. See *Cancer Chemotherapy: Principles and Practice,* ed. B. A. Chabner, J. M. Collins, Phil., Lippincott Publ., 1990; *Cancer: Principles and Practice of Oncology;* ed. de Vita, Jr., V. T., Hellman, S., and Rosenberg, S. A., Lippincott Co., Philadelphia, 1993; *The Chemotherapy Source Book,* ed. Perry, M. C., Williams and Wilkins Publ., Baltimore, 1991). Silverman, Richard B., The Organic Chemistry of Drug Design and Drug Action, Academic Press, Inc. N.Y. (1992); Smith, Michael B., Organic Synthesis, McGraw Hill, Inc., N.Y., (1994)).

Methods are well known in the art for determining therapeutically effective amounts of the compounds used in the method of the invention. Such methods involve analysis of the pharmaceutical/pharmacokinetic parameters in anti-cancer or antitumor therapy, i.e for inhibiting the growth of cancerous tumors (Wedge. S. R., Porteus, J. K., Newlands, E. S., *Cancer Chemother, Pharmacol.* (1997) 40:266–272; Legha, S. S., *Seminar in Oncology,* (1997) 24:S4-24–31; Motzer, R. J., Vogelzang, N. J., Chemotherapy for Renal Cell Carcinoma. In: Raghaven, D., Scher, H. I., Leibel, S. A., et al: eds. *Principles and Practice of Genitourinary Oncology,* Lippincott-Raven Publ., Philadelphia, pp. 885–96, 1997; Bloom, H. J., Medroxyprogesterone acetate (Provera) in the treatment of metastatic renal cancer, *Br. J. Cancer* (1971) 25:250–65)

The present invention shows that in the presence of 6,6'-dithiodinicotinic acid the mutagenic effect of carcinogenic chemicals, exemplified by benzo-[a]-pyrene, 2-aflatoxin, and 2-aminofluorene, is greatly diminished.

6,6'-dithiodinicotinic acid (carboxypyridine disulfide, CPDS) (D. R. Grassetti, 1986, Drugs of the Future, 1 1(7):559–61) is known to prevent metastases in mice (Grassetti, D. R., 1970, Nature 228:282).

Examples 1, 2, and 3 report experiments in which the antimutagenic effects of 6,6'-dithiodinicotinic acid were observed. These experiments were performed with a mutant strain of Salmonella Typhimurium bacteria T-100. When the cells were exposed to varying amounts of benzo-[a]-pyrene, 2-aflatoxin, or 2-aminofluorene, a number of colonies (mutant) were formed. When 6,6'-dithiodinicotinic acid was present in the culture prior to the addition of carcinogen, the number of mutants decreased by about 70%.

As shown in Example 4 below, a method of the present invention is based on the finding that 6,6'-dithiodinicotinic acid inhibited the activity of poly(ADP-ribose) polymerase (ADPRP). Inhibition of ADPRP is useful for blocking the mutagenic effects of carcinogens (Suto and Suto (1991), Drugs of the Future, 16(8):723–739). It is understood that 6,6'-dithiodinicotinic acid includes derivatives thereof, including, but not limited to alkaline metal salts and alkyl esters.

The method of the present invention includes administering a pharmaceutical composition comprising an effective amount of 6,6'-dithiodinicotinic acid in pure form or as a pharmaceutically acceptable crude concentrate in association with a pharmaceutical carrier or diluent. Such compositions conveniently contain less than 1% by weight, and preferably about 0.2% by weight, of 6,6'-dithiodinicotinic acid, and involve administration of at least about 0.1 mg/kilo of body weight of 6,6'-dithiodinicotinic acid. The compositions may be prepared by conventional techniques to be in conventional forms, for example, capsules, tablets, suppositories, dispersible powders, syrups, elixirs, suspensions or solutions for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period. Other compounds and methods known in the art for delaying disintegration or for timed-delayed or time-measured delivery of the active ingredients also find use in formulating the active ingredients for use in the methods of the invention. For example, 6,6'-dithiodinicotinic acid may also be combined with liposomes or other delayed-release carrier means to protect the compounds from degradation until they reach their targets and/or facilitate movement of the compounds across tissue barriers.

The preferred compositions from the standpoint of ease of administration are solid compositions, particularly solid-filled gelatin capsules or tablets.

The carcinogens tested here are representative of the carcinogens which form a major part of air pollutants caused by tobacco smoke, the exhaust fumes of internal combustion engines, among other sources.

It has been observed that 6,6'-dithiodinicotinic acid is not a toxic compound. It can be taken in doses of at least approximately 0.1 gram per day for indefinite periods. This fills the requirements for a non-toxic, low-cost chemopreventive agent, which could be administered orally.

LEGEND TO TABLES 1, 2, 3

The effect of 6,6'-dithiodinicotinic acid (0.3 mg/plate, in 0.2M sodium bicarbonate) added to each plate in the Ames test, which is a reverse mutation assay (Ames, B. N. et al, 1975, Mutation Research 31:347) with Salmonella Typhimurium bacteria T-100 was studied. The 6,6'-dithiodinicotinic acid was added to each plate one hour before the addition of the carcinogen. The results reported in the tables represent the average values (number of colonies per plate) of 3 individual determinations.

EXAMPLE 1

EFFECTS OF 6,6'-DITHIODINICOTINIC ACID ON MUTAGENESIS BY BENZO-[a]-PYRENE

Number of Colonies Per Plate

| Benzo-[a]-pyrene (μg/plate) | No inhibitor | With Inhibitor | Decrease (%) |
|---|---|---|---|
| 0(control) | 100 | 111 | 0 |
| 2.5 | 1286 | 339 | 74 |
| 5.0 | 1171 | 446 | 62 |
| 10.0 | 1130 | 488 | 58 |

EXAMPLE 2

EFFECTS OF 6,6'-DITHIODINICOTINIC ACID ON MUTAGENESIS BY 2-AMINOFLUORENE

Number of Colonies Per Plate

| 2-Aminofluorene (μg/plate) | No Inhibitor | With Inhibitor | Decrease (%) |
|---|---|---|---|
| 0(control) | 149 | 141 | 0 |
| 5.0 | 773 | 705 | 10 |
| 15.0 | 2295 | 655 | 72 |
| 25.0 | 2134 | 791 | 63 |

EXAMPLE 3

EFFECTS OF 6,6'-DITHIODINICOTINIC ACID ON MUTAGENESIS BY 2-AFLATOXIN

Number of Colonies Per Plate

| 2-Aflatoxin (μg/plate) | No Inhibitor | With Inhibitor | Decrease (%) |
|---|---|---|---|
| 0 (control) | 108 | 104 | 0 |
| 20 | 504 | 188 | 63 |
| 50 | 1117 | 358 | 68 |
| 100 | 1662 | 471 | 72 |

EXAMPLE 4

INHIBITION OF ADPRP BY 6,6'-DITHIODINICOTINIC ACID

ADPRP was prepared from pig thymus using the method of Khan and Shall (Biochem. Soc. Transactions 4:778 (1976)) with various modifications. Enzyme activity was approximately linear up to 15–20 minutes with NAD substrate concentration of 25 μM. Typical maximum enzyme activity was around 0.003 μmol product formed/minute in the assay (i.e. approximately 0.1 % of substrate utilized). $K_M$ was approximately 25 μM.

Using a standard assay mix containing 2 mM dithiothreitol (DTT) and 100 μM crude enzyme/ml incubation, three experiments were performed with 6,6'-dithiodinicotinic acid added at concentrations varying from 5 μg/ml to 600 μg/ml (i.e. 1/60th molar equivalent of DTT to 2 molar equivalents). Significant and specific inhibition of ADPRP by 6,6'-dithiodinicotinic acid was seen at 50 μg/ml with almost complete inhibition at 150 μg/ml and above (i.e. 0.5 molar equivalents of DTT and above). No inhibition was seen at 5 and 25 μg/ml. The addition of excess DTT to an incubation containing 150 μg/ml 6,6'-dithiodinicotinic acid did not increase the extent of conversion of substrate to bound product.

INHIBITION % OF CONTROLS

| Concn of 6,6'-dithiodinicotinic acid (µg/ml) | Percent Inhibition at: | | |
|---|---|---|---|
| | 7.5 min. | 15 min. | 20 min. |
| 5 | 0 | 14 | — |
| 25 | 0 | 0 | — |
| 50 | 37 | 38 | — |
| 100 | 68 | 54 | — |
| 150 | 88 | 70 | 90 |
| 300 | — | — | 93 |
| 600 | — | — | 83 |

These are values for individual incubations which were stopped at either 7.5, 15, or 20 minutes. These results indicate that 6,6'-dithiodinicotinic acid is an effective inhibitor of ADPRP, forming the basis of the method of the invention for treating a human subject to inhibit mutagenic effects of carcinogens by administering to a human subject a composition comprising a sufficient amount of 6,6'-dithiodinicotinic acid (or derivatives thereof) to inhibit activity of ADPRP in the subjects in order to inhibit the mutagenic effects of the carcinogens. Alternatively, the invention also directs itself to a method of inhibiting ADPRP in a human subject in order to inhibit the mutagenic effects of carcinogens, the method involving administering to a human subject a composition comprising a sufficient amount of 6,6'-dithiodinicotinic acid (or derivatives thereof) to specifically inhibit activity of ADPRP in the subjects in order to inhibit the mutagenic effects of the carcinogens.

Having thus described exemplary embodiments of the present invention, it should be noted by those skilled in the art that the disclosures herein are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method of treating a human subject to inhibit mutagenic effects of carcinogens in said subject wherein the method comprises administering to said subject a composition comprising a sufficient amount of 6,6'-dithiodinicotinic acid to specifically inhibit activity of poly(ADP-ribose) polymerase in said subject to thereby inhibit said effects.

2. The method of claim 1 wherein a sufficient amount of 6,6'-dithiodinicotinic acid is at least 0.1 mg/kilo of body weight.

3. A method of specifically inhibiting poly(ADP-ribose) polymerase in a human subject to inhibit the mutagenic effects of carcinogens on said subject, said method comprising administering to said subject a composition comprising a sufficient amount of 6,6'-dithiodinicotinic acid to said human to thereby inhibit said effects.

4. The method of claim 3 wherein a sufficient amount of 6,6'-dithiodinicotinic acid is at least 0.1 mg/kilo of body weight.

* * * * *